United States Patent
Mapes et al.

(10) Patent No.: US 7,189,516 B2
(45) Date of Patent: Mar. 13, 2007

(54) METHOD FOR CHARACTERIZING AUTOIMMUNE DISORDERS

(75) Inventors: James P. Mapes, Austin, TX (US); James W. Jacobson, Austin, TX (US); Harold N. Baker, Austin, TX (US); Michael D. Spain, Austin, TX (US)

(73) Assignee: Luminex Corporation, Austin, TX (US)

( * ) Notice: Subject to any disclaimer, the term of this patent is extended or adjusted under 35 U.S.C. 154(b) by 467 days.

(21) Appl. No.: 10/222,867

(22) Filed: Aug. 19, 2002

(65) Prior Publication Data

US 2003/0087326 A1     May 8, 2003

Related U.S. Application Data

(60) Provisional application No. 60/312,746, filed on Aug. 17, 2001.

(51) Int. Cl.
*G01N 33/53*     (2006.01)

(52) U.S. Cl. ................. 435/7.1; 435/7.92; 435/973; 436/506; 436/518; 436/523; 436/524

(58) Field of Classification Search ............... 435/7.1, 435/7.92–7.95, 973; 436/501, 518, 523, 436/524, 164, 811, 506
See application file for complete search history.

(56) References Cited

U.S. PATENT DOCUMENTS

| | | | |
|---|---|---|---|
| 5,200,318 A * | 4/1993 | Rabin et al. ............... 435/7.21 |
| 5,561,049 A | 10/1996 | Vold et al. | |
| 5,811,233 A * | 9/1998 | Bowcock et al. ............... 435/6 |
| 5,981,180 A | 11/1999 | Chandler et al. | |
| 6,211,352 B1 * | 4/2001 | Harrison et al. ........... 536/23.2 |
| 6,391,651 B1 * | 5/2002 | Maclaren et al. ........... 436/506 |
| 2005/0106633 A1 * | 5/2005 | Baekkeskov et al. ........ 435/7.2 |

OTHER PUBLICATIONS

Beers et al., The Merck Manual of Diagnosis and Therapy, 17th edition, 1999, pp. 1061-1067.*
Gudjonsson et al., Immunopathogenic mechanisms in psoriasis, Clin Exp Immunol 2004; 135, pp. 1-8.*
International Search Report, International Application No. PCT/US02/26267, International Filing Date Aug. 19, 2002.

* cited by examiner

*Primary Examiner*—Long V. Le
*Assistant Examiner*—Gary W. Counts
(74) *Attorney, Agent, or Firm*—Mollie E. Lettang; Charles D. Huston; Daffer McDaniel, LLP

(57) ABSTRACT

The invention relates to methods of characterizing autoimmune diseases by detecting and measuring at least one analyte using multiplexed assay systems. According to one embodiment, a target is detected and measured by different bead sets having different reactants. According to another approach the ratio of self-antigen to autoantibody is measured by exposing a sample suspected of containing self-antigen and autoantibody to a bead set associated with monoclonal antibody specific for the self-antigen and a bead set associated with the self-antigen.

8 Claims, No Drawings

METHOD FOR CHARACTERIZING AUTOIMMUNE DISORDERS

1.0 RELATED APPLICATIONS

This application claims priority to U.S. Provisional Application No. 60/312,746, filed Aug. 17, 2001, which is incorporated herein by reference.

2.0 FIELD OF THE INVENTION

The present invention relates generally to methods of, and products for, measurement of varied targets in biological fluids. The present invention relates, more specifically, to rapid assays for diagnosis of autoimmune diseases.

3.0 BACKGROUND OF THE INVENTION

Analysis of clinical specimens is important in science and medicine. Multiplexed assays to determine qualitative and/or quantitative characteristics of a specimen are known in the art. For example, U.S. Pat. No. 5,981,180 (the "'180 patent"), which is hereby incorporated by reference, discloses methods, instrumentation, and products for detecting multiple analytes in a fluid sample by flow cytometric analysis. The products include bead subsets, each bead subset having a different reactant bound to the bead. The individual subsets are prepared so that beads within a subset are relatively homogenous but differ in at least one distinguishing characteristic from beads in any other subset. Therefore, the subset to which a bead belongs can readily be determined after beads from different subsets are pooled. The methods include pooling the variously labeled subsets prior to assay and mixing the pooled bead set with a fluid sample to test for analytes reactive with the various reactants bound to the beads.

Autoimmunity is a disease condition whereby the body's immune system produces autoantibodies against the body's own normal components, i.e. self-antigens, rather than antibodies against foreign substances, i.e. antigens, to the body. The onset of autoimmune disorder is difficult to diagnose because autoantibodies may be produced from about one month prior to as much as thirty years prior to development of such a disorder. As a result, conducting clinical trials for pharmaceuticals directed to preventing autoimmune disorder is problematic; it is economically and logistically prohibitive to run trials for an unknown length of time and up to thirty years in duration.

There is therefore a need for a method which can better define clinical presentation of autoimmune disorders. Preferably, such a method could enable researchers to identify those patients that would develop disorders in the short term and thus be suitable candidates for clinical trials.

4.0 SUMMARY OF THE INVENTION

The present invention teaches a novel approach to the differential diagnosis and/or analysis of many autoimmune diseases. Generally, the invention relates to detecting, in a sample, for example of blood, drawn from a patient, the ratio of autoantibody to self-antigen, the presence of self-antigen and variations of the self-antigen, the varied autoantibodies specific for a self-antigen, and/or the relative amount of autoantibody bound to self-antigen.

In one aspect, the present invention relates to a method of analyzing autoimmune disease states, comprising: determining a first ratio of autoantibody to self-antigen in a first sample of blood from a patient by: (a) exposing the blood sample to a pooled population of subsets of particles, wherein at least one subset of particles is bound to a reactant capable of binding the autoantibody and at least one subset of particles is bound to a reactant capable of binding the self-antigen; and (b) detecting the amount of autoantibody and the amount of self-antigen in the blood sample. In some embodiments, the reactant capable of binding the autoantibody is the self-antigen itself, whereas the reactant capable of binding the self-antigen is a monoclonal antibody to the self-antigen. In some embodiments of the invention, the ratio is compared against standard ratios representing normal and differing degrees of disease states for the disease being analyzed to determine the presence, absence, onset, or progression of the disease. In some embodiments, the method is repeated over time and the derived ratios are compared one to another to analyze the presence, absence, onset, or progression of the disease.

In one embodiment, therefore, the method includes determining a second ratio of autoantibody to self-antigen in a second sample of blood from the same patient. The second sample is drawn subsequently in time to the first sample. Such a method also includes comparing the second ratio to the first ratio to analyze the presence, absence, onset, or progression of disease. In another embodiment, the method includes determining at least one subsequent ratio of autoantibody to self-antigen in at least one additional sample of blood from the same patient. Each of the at least one additional sample of blood is drawn subsequently in time from the previous sample. Such a method also includes comparing the at least one subsequent ratio to the first ratio to analyze the presence, absence, onset, or progression of disease.

In one aspect, the present invention relates to a method of detecting a condition indicative of a disease state comprising, (a) providing a pooled population of subsets of particles, wherein the particles of one subset: (i) are distinguishable from the particles of another subset based at least on the fluorescence characteristic of the particles; and (ii) are associated with a reactant capable of binding an analyte related to the disease state, wherein the reactant associated with one subset of particles is different from the reactant associated with another subset of particles; (b) exposing a sample containing at least one analyte related to the disease state to the pooled population of subsets of particles to enable the at least one analyte to react with a corresponding reactant; and (c) simultaneously detecting an amount of analyte associated with each subset of particles. In some embodiments, the analytes of interest are a self-antigen and its corresponding autoantibody or autoantibodies. In some embodiments, the analytes of interest are the variations of the self-antigen and may also be the self-antigen. In some embodiments, the analytes of interest are the autoantibodies corresponding to a self-antigen.

In one aspect, the present invention relates to a process for measuring, in a sample, the ratio of an autoantibody to an antigen comprising: (a) exposing the sample to a plurality of assay systems, (b) detecting the amounts of the autoantibody and the antigen, and (c) comparing the amounts of the autoantibody to antigen. A particular sample can have an absence, a presence, or a measurable amount of the autoantibody or of the antigen or both. The sample can be a biological fluid or suspension. The biological fluid or suspension can include, but is not limited to, blood, serum, plasma, sweat, tears, urine, sputum, saliva, semen, cerebrospinal fluid, alveolar fluid, lung lavage, gastric fluid, gastric lavage, peritoneal fluid, wound fluid, nasal discharge, bone marrow sample, cyst fluid, or combinations thereof. The biological fluid or suspension can be used after dilution with an acceptable diluent, which can be saline.

In one aspect, the present invention relates to a pooled population of subsets of particles for use in detecting conditions associated with autoimmune disease. In some embodiments, the particles are beads, which are associated with a reactant specific for an analyte of interest and are suitable for use in flow cytometry experiments; the subsets of particles are distinguishable from one another at least by their fluorescence characteristic; and the pooled population comprises at least two subsets of particles, the first subset of particles being associated with a first reactant, which is a monoclonal antibody specific for a self-antigen, the second subset of particles being associated with a second reactant, which is the self-antigen.

Specific embodiments of the present invention may be directed to one, some or all of the above-indicated aspects as well as other aspects, and may encompass one, some or all of the above- and below-indicated embodiments as well as other embodiments. Thus, for example, a method according to the present invention may comprise predicting the onset of type I diabetes mellitus by repeatedly measuring the ratio of autoantibody to insulin over time, wherein the ratio is measured by using a pooled subset of particles in a flow cytometry experiment according to, for example, the '180 patent, wherein a first subset is a set of beads associated with a monoclonal antibody specific for insulin and a second subset is a set of beads associated with insulin.

5.0 DETAILED DESCRIPTION OF SPECIFIC EMBODIMENTS

5.1 Definitions

The term "particle" refers to a solid phase material, such as a microsphere or bead, suitable for use in flow cytometric multiplexed assays, for example assays in accordance with the '180 patent.

The term "subset of particles" refers to a group of particles sharing essentially the same characteristic classification parameters. By "essentially" it is mean that the particles are similar to the extent that they can be identified as belonging to the same subset of particles and also distinguished from the particles of another subset. One subset of particles is distinguishable from another at least based on its fluorescent characteristic and on the reactant bound to it.

The term "reactant" refers to a substance associated with the microsphere or bead, generally bound to the surface of the microsphere or bead, that is capable of coupling with an analyte of interest, suspected of being in the sample to be analyzed. Thus, for example, the reactant might be insulin, which is capable of coupling to its autoantibody. Or else the reactant might be a monoclonal antibody specific for insulin.

The term "analyte," "analyte of interest," "target," and "target of interest" are used interchangeably to refer to a substance desired to be measured and suspected of being present in the sample to be analyzed. Thus, for example, if it is desired to measure the amount of insulin and the amount insulin autoantibody in a sample to obtain a ratio of insulin to autoantibody, both the insulin and insulin autoantibody are "analytes," "analytes of interest," "targets" or "targets of interest." It is understood that when, for example, a self-antigen such as insulin is the "target," the particle associated with a reactant specific for that self-antigen may also bind to a self-antigen which is already complexed with an autoantibody. Thus, when the target is a self-antigen, it is understood that the target is also the self-antigen/autoantibody complex.

The phrase "variations of a target" refers, for example either to the cells which produce the analyte, or mutations/variations of the analyte that can be produced, for example, by dying cells. For example, if insulin is a target, variations of insulin would include the cell which produces insulin or altered forms of insulin which may be produced by dying cells.

The phrase "multiplexed assay" refers to an assay, such as those described in the '180 patent, capable of making different measurements simultaneously. "Different measurements" is understood to mean detection of multiple analytes, or detection of a single analyte by different bead subsets, or a combination of both. In this context, "simultaneously," is understood to mean that the multiple analytes are detected, or the single analyte is detected by different bead sets, or the combination of measurements, is performed in the same assay, for example in the same flow cytometric run. Typically, a multiplexed assay will be performed in a single vessel containing several sets of particles (i.e. pooled subsets of particles), such that a single multiplexed assay will provide multiple read-outs of information. Thus, the multiplexed assay of the '180 patent is an example of the application of simultaneous analysis.

5.2 Description

The present invention relates to the measurement of varied targets present in the blood of individuals predisposed to or exhibiting various forms of a disorder. The inventive methods may be useful in a better definition of clinical presentation of disorders associated with the targets measured.

Disorders which can be characterized by methods according to the present invention include autoimmune diseases such as, for example, type I diabetes mellitus, Grave's disease, psoriasis, Duchenne's muscular dystrophy, Hashimoto's thyroiditis, systemic lupus erythematosis, rheumatoid arthritis, scleroderma, Sjögren's syndrome, ulcerative colitis, Crohn's disease, silicone implant-induced autoimmune reaction, immune deficiency syndrome, autoimmune hepatitis, Takayasu's arthritis, phagoneuroglanulomatosis, myasthenia gravis, cirrhosis, Birdshot retinopathy, or anticoagulant deficiency due to autoantibodies. However, the invention is not limited to characterizing autoimmune disorders and can be applied to disorders involving circulating antigens.

Generally, the invention is directed to methods for characterizing a disorder comprising analyzing a sample comprising at least one analyte by a multiplexed assay system. In one embodiment, the multiplexed assay system can comprise a pooled population of at least two subsets of particles, wherein the particles of each subset bind the same analyte but the particles of one subset are associated with a reactant specific for the analyte and the particles of another subset are associated with a different reactant specific for the same analyte. For example, the particles of one subset may be bound to a first autoantibody capable of binding a self-antigen and the particles of another subset are bound to a second autoantibody capable of binding a self-antigen. A sample containing the self-antigen could then be analyzed by multiplexed flow cytometric analysis, such as described in the '180 patent, and results, which may be indicative of the relative affinities of the autoantibodies to the self-antigen could provide better definition of the clinical presentation of the disease.

In an alternative embodiment, the multiplexed assay comprises at least two subsets of particles, the particles of a first subset are associated with a reactant specific for the self-antigen, for example a monoclonal antibody specific for the self-antigen, and the particles of the second subset are associated with a reactant specific for the autoantibody, that is the particles are associated with the self-antigen itself. The multiplexed assay could then be used to detect and measure amounts of autoantibody, self-antigen (including self-antigen/autoantibody complex) in a sample suspected of containing the autoantibody and self-antigen. The ratio of autoantibody to self-antigen derived from the measurement could provide better definition of the clinical presentation of the disease.

In an alternative embodiment, the multiplexed assay could perform both assays described above. That is, the multiplexed assay could comprise at least at least four subsets of particles, the particles of a first subset would be associated with a self-antigen, the particles of a second subset would be associated with monoclonal antibody specific for the self-antigen, the particles of a third subset would be associated with a first autoantibody to the self-antigen, and the particles of fourth subset would be associated with a second autoantibody to the self-antigen. Of course, as many subsets as different autoantibodies could be used.

For example, a method according to the present invention could be used to measure the ratio of varied targets present in the blood of individuals predisposed to or exhibiting the autoimmune disease Type I Diabetes mellitus. Repeated measurements over time, indicating an increased amount of autoantibody relative to insulin, could be used to predict onset of diabetes. In an embodiment of the method a pooled population of subsets of particles would be used to measure the ratio of autoantibody to insulin. Particles of one subset would be associated with insulin, which would bind autoantibody in the sample to be analyzed. Particles of another subset would be associated with a monoclonal antibody to insulin, which would bind insulin and insulin/autoantibody complex in solution. The ratio so measured can be compared to a standard in which the standard can include a reference value for the disease or a previously measured ratio for that same patient. With respect to the latter, over time, a change in the measured ratio, specifically a higher ratio of autoantibody to insulin, may indicate depletion of insulin and onset or presence of disease.

Without being bound by theory, the methods are based on the notion that blood from individuals predisposed to or exhibiting various forms of a disorder may present a target in at least two forms that can be appropriately measured using well-characterized immunoassay techniques. Autoimmune disorders represent an example of such a concept. Nascent autoantibodies present in an autoimmune disorder should have several populations of antibodies present in the serum. It is postulated that for one such population the antibodies are tightly bound to the agent responsible for the development of the autoimmune disorder. It is further postulated that also present is another population that may be more loosely bound to the agent or that may not be bound to any of the agent present in the blood. It is further postulated that the rapid measurement of both types of antibody populations will lead to a better prediction of the clinical condition of the patient. This can be accomplished by attaching the target of such a disorder or its associated antibody to a solid phase for separate assays of the contents of the blood. As a further extension of this principle, additional antibodies to a target and/or variations of a target may be added to additional solid phases for a more complete evaluation of the agents present in a sample of blood from a patient.

The initial observation has been made with insulin autoantibodies in serum from individuals predisposed to the development of Type I Diabetes mellitus. Type I Diabetes mellitus has been described as an autoimmune disorder. In an experiment performed to demonstrate this concept, insulin was coupled to one set of beads and a monoclonal antibody to insulin was coupled to a second set of beads. A mixture of these beads (i.e. pooled population of subsets of particles) was then used in an assay to measure the presence of autoantibodies to insulin. Two distinct populations could be observed in each serum sample. The two populations also varied among the individual samples assayed. In some of the samples there was a stronger response to the beads to which insulin-was coupled. In other samples there was a stronger response to the beads to which the antibody to insulin was coupled. The pattern observed in an assay with the mixed set of beads matched the pattern observed in assays when each set of beads was used individually. The observed phenomenon may be indicative of a depletion or loss of circulating insulin sequestered by the autoantibodies. Changes in ratios of unbound to bound insulin may represent a temporal linear progression toward complete manifestation of diabetes.

The phenomenon observed for diabetes should be exhibited in any and all autoimmune disorders involving circulating antigens and the above-described methodology is a unique example of a technique that can appropriately measure the components present in an autoimmune disorder. Additional targets, including tumor markers (i.e. tumor antigens), hormones, etc., which may be present in the blood in both a bound and free form may also benefit from application of methods according to this invention. For example, the tumor marker PSA can be found in bound and unbound form, the bound form being PSA bound to a protein that carries it around the body non-specifically. The disease state, prostate cancer, associated with PSA could therefore be better defined by applying the inventive methodology to analyzing samples suspected of containing PSA. Thus, for example, a sample of blood, drawn from a patient, could be analyzed by multiplexed flow cytometric analysis using a subset of beads associated with PSA and a subset of beads associated with a monoclonal antibody specific to PSA. A ratio of PSA to autoantibody could be derived from those measurements. As with the insulin example above, if samples are taken from a patient over time and analyzed a change in ratio may be indicative of a change in disease state.

As described above, additional antibodies to a target and/or variations of a target may be added to create additional sets of beads to further enhance the assay for an autoimmune disorder, tumor marker, hormone, etc. The different populations of these targets in a blood sample can be measured concurrently and temporally, using for example the flow cytometric analysis described in the '180 patent, for a more complete description of the characteristics of a disorder associated with the targets measured. Therefore, the inventive methods can be useful in a better definition of clinical presentation of disorders associated with the targets measured.

Another aspect of the present invention is kits for the detection or quantitation of an analyte or analytes. The kits can comprise pooled subsets of particles suitable for characterizing disorders. For example, the kit could include a first and second subset of particles. The particles of the first subset are associated with a first reactant, a self-antigen, whereas the particles of the second subset are associated with a second reactant, a monoclonal antibody to that self-antigen. The particles, apart from the reactant, can be polymeric particles which range in size from 0.01 to 1000 micrometers (μm) in diameter. In one embodiment, the size ranges from 0.1–500 μm. In another embodiment the size ranges from 1–200 μm. In another embodiment the size ranges from 2–12 μm. The particles can be similarly-sized. By "similarly-sized," it is meant that difference between particles within a set is not more than 15%. The particles can be of any shape. In one embodiment, the shape is globular. However, particles of any other shape can be employed. The shape of the particle can serve as an additional distinction parameter, which can be discriminated by flow cytometry, e.g., by high-resolution slit-scanning or by light scatter.

The kits can include signal ligands for use with sandwich or competitive immunoassays. A signal ligand refers to a reactant, which is unassociated to any bead, capable of binding a target and being detected. A signal ligand can be, for example, any substance having associated therewith a detectable label such as a fluorescently- or radioactively-tagged antibody or antigen. The kit can also contain a binding partner for the signal ligand which forms a complex with for example, an antibody, antigen, biotin, hapten, or analyte. The kits can include sets of particles for use as internal standards. Or else the kits can includes a set or sets of particles for use as controls. Or else the kits can include sets of particles for use as internal standards and a set or sets of particles for use as controls.

A person of ordinary skill will appreciate that changes could be made to the embodiments described above without departing from the broad inventive concept thereof. It is understood, therefore, that this invention is not limited to the particular embodiments disclosed, but it is intended to cover modifications within the spirit and scope of the invention.

For example, although analysis of blood drawn from a patient suspected of having a disease or being predisposed to a disease, is principally described, the multiplexed analysis could be performed on samples containing controlled amounts of target relating to the disease conditions. For example, if a sample containing a controlled amount of self-antigen is exposed to a pooled subset of particles, wherein the particles of each of the subsets was associated with a different reactant, but each of the reactants was specific for the same analyte, for example each subset was associated with a different autoantibody for a self-antigen, then the relative affinity of a self-antigen to varying autoantibodies may be determined.

Also, although the illustrated embodiments are particularly adapted for use with addressable microsphere technology developed by Luminex Corporation, and disclosed for example in U.S. Pat. No. 5,981,180, the present invention can be adapted for use with any multiplexed assay system.

6.0 EXAMPLES

The following examples are for illustrative purposes only; the scope of the invention is not in any way limited to the particular examples provided.

6.1 Application of the Methods of the Invention to Diabetes Mellitus, Type I

Serum samples from individuals predisposed to the development of Type I Diabetes mellitus are tested for insulin autoantibodies by the methods and compositions of the invention. Type I Diabetes mellitus has been described as an autoimmune disorder. In an experiment performed to demonstrate the method of the invention, insulin is coupled to one set of Luminex Beads and a monoclonal antibody to insulin is coupled to a second set of Luminex Beads. A mixture of these beads is then used in an assay to measure the presence of autoantibodies to insulin by sandwich assays in a fluorescence cytometer. Two distinct populations can be observed in each serum sample. It is further observed that these two populations varied among the individual samples assayed. In some of the samples a stronger response is exhibited to the beads to which insulin was coupled. In other samples a stronger response is exhibited to the beads to which the antibody to insulin was coupled. The pattern observed in an assay with the mixed set of beads matches the pattern observed in assays when each set of beads is used individually.

The observed phenomenon can be indicative of a depletion or loss of circulating insulin sequestered by the autoantibodies. Changes in the ratios of the unbound to bound insulin can represent a temporal linear progression toward complete manifestation of diabetes.

6.2 Autoantibodies in Diabetes Mellitus, Type I.

Children with diabetes mellitus, type I, commonly have, in the blood, circulating autoantibodies to glutamate decarboxylase, autoantibodies to the cells of the islets of Langerhans, and/or autoantibodies to insulin. Relatives of such patients have a lower frequency of these autoantibodies. The pathogenesis of diabetes mellitus, type I, appears to develop as an activation of autoimmunity in persons with genetic predisposition and may be influenced by environmental factors. An early stage of the pathogenesis is the lymphocytic infiltration of the pancreatic islets of Langerhans, followed by destruction of pancreatic beta cells by cytotoxic T lymphocytes. A very early and specific response is the development of immunoreactivity to glutamate decarboxylase. Another early response is the development of immunoreactivity to insulin. Another early response is the elicitation of antibodies termed IA-2 (insulinoma-associated protein-2/protein tyrosine phosphatase).

Multiple subsets of particles are prepared each with an identifiable red to orange fluorescence ratio. One subset is conjugated to insulin by standard methods. A second subset is conjugated to glutamate decarboxylase. A third subset is conjugated to IA-2. The subsets are combined and an aliquot combined with a serum sample from each of several children at risk for developing diabetes mellitus, type I. After a short incubation, fluorescein-labeled anti-human (IgG+IgM) is added and the samples can also be mixed with internal standards consisting of known amounts of autoantibodies (to insulin, glutamate decarboxylase and IA-2) conjugated to particles, to provide absolute values for the amount of auto antibodies.

6.3 Analysis of Autoantibodies as a Component of Experimental Diagnosis of Graves'Disease Distinct and identifiable subsets particles are prepared: one subset conjugated to human thyroid microsomal peroxidase (TPO); one subset to the flavoprotein subunit of succinate dehydrogenase; one subset conjugated to the extracellular domain of the human TSH receptor or the C-terminal region thereof; and one subset conjugated to tumor suppressor gene p53. Serum samples of women with familial histories of Graves'disease and/or Hashimoto's thyroiditis are tested with an aliquot of the pooled particles and a signal molecule in which a fluorescein—conjugated anti-human (IgG+IgM) immunoglobulin G is used. An internal standard is used to quantify autoantibody levels. The quantitative results are compared to standard individual radio-immunoassays and a physical diagnosis.

6.4 Multiple Clonal Autoantibodies to the TSH Receptor in Conjunction with Graves'Disease The method of Example 6.3 is used with the variation that several subsets of particles are prepared each comprising a different short fragment of the C-terminal region of the extra cellular domain of the TSH receptor. The custom oligopeptides of the C-terminal region are obtained from a commercial source (e.g. Bachem) and conjugated to the particle by any standard method.

We claim:

1. A method for analyzing the progression of an autoimmune disease associated with autoantibodies in a patient, comprising:
    exposing a first sample of biological fluid from the patient to a pooled population of particles, wherein at least one first subset of the pooled population of particles is bound to a first reactant that binds an autoantibody and at least one second subset of the pooled population of particles is bound to a second reactant that binds a self antigen;
    measuring an amount of autoantibody in the first sample of biological fluid;
    measuring an amount of self-antigen in the first sample of biological fluid;
    determining a first ratio of the measured amount of autoantibody to the measured amount of self-antigen
    determining a second ratio of autoantibody to self-antigen in a second sample of biological fluid taken from the same patient as the first sample of biological fluid, wherein the second sample of biological fluid is drawn subsequent to the first sample of biological fluid; and
    comparing the second ratio to the first ratio to analyze the progression of the autoimmune disease in the patient, wherein the autoimmune disease:
        has progressed further on condition that the second ratio is greater than the first ratio.

2. The method according to claim 1, wherein the first reactant that binds the autoantibody is the self-antigen, and wherein the second reactant that binds the self-antigen is a monoclonal antibody specific for the self antigen.

3. The method according to claim 2, wherein the self antigen is insulin.

4. The method according to claim 1, further comprising comparing at least one of the first and second ratios to one or more standard ratios representing differing states of the autoimmune disease to determine states of the autoimmune disease in the respective first and second samples.

5. The method according to claim 1, further comprising:
    determining at least one subsequent ratio of autoantibody to self-antigen in at least one additional sample of biological fluid taken from the same patient as the first and second samples, wherein each of the at least one additional sample of biological fluid is drawn subsequently in time from the previous samples; and
    comparing the at least one subsequent ratio to the previous ratios to further analyze the progression of the autoimmune disease in the patient, wherein the autoimmune disease; has progressed further on condition that the subsequent ratio is greater than the previous ratios.

6. The method according to claim 1, wherein the autoimmune disease is selected from a group consisting of type I diabetes mellitus, Grave's disease, psoriasis, Duchenne's muscular dystrophy, Hashimoto's thyroditis, systemic lupus erythematosis, rheumatoid arthritis, scleroderma, Sjogren's syndrome, ulcerative colitis, Crohn's disease, silicon implant-induced autoimmune reaction, immune deficiency syndrome, Takayasu's arthritis, phagoneuroglanulomatosis, nyasthenia gravis, cirrhosis, Birdshot retinopathy, and anticoagulant deficiency due to autoantibodies.

7. The method according to claim 1, wherein the step of measuring the amount of self-antigen within the first sample of biological fluid comprises measuring a concentration of self-antigen bound to the autoantibody and a concentration of unbound self-antigen.

8. The method according to claim 7, further comprising:
    determining a third ratio of the amount of unbound self-antigen in the first sample of biological fluid to the amount of bound self antigen in the first sample of biological fluid;
    determining a fourth ratio of the amount of unbound self-antigen in the second sample of biological fluid to the amount of bound self-antigen in the second sample of biological fluid; and
    comparing the fourth ratio to the third ratio to analyze the progression of the autoimmune disease in the patient, wherein the autoimmune disease: has progressed further on condition that the fourth ratio is greater than the third ratio.

* * * * *